US012736550B2

(12) United States Patent
Bao et al.

(10) Patent No.: US 12,736,550 B2
(45) Date of Patent: Sep. 15, 2026

(54) SEPARATING APPARATUS OF BIOSUBSTANCE AND SEPARATING METHOD OF THE SAME

(71) Applicants: INVENTEC EASY DOCTOR CORPORATION, Shanghai (CN); INVENTEC APPLIANCES (PUDONG) CORPORATION, Shanghai (CN); INVENTEC APPLIANCES (SHANGHAI) CO. LTD., Shanghai (CN); INVENTEC APPLIANCES CORPORATION, New Taipei City (TW)

(72) Inventors: Ling-Yan Bao, Shanghai (CN); Wei-Shan Hung, New Taipei City (TW)

(73) Assignee: INVENTEC APPLIANCES CORPORATION, New Taipei City (TW)

( * ) Notice: Subject to any disclaimer, the term of this patent is extended or adjusted under 35 U.S.C. 154(b) by 992 days.

(21) Appl. No.: 17/968,259

(22) Filed: Oct. 18, 2022

(65) Prior Publication Data

US 2023/0118289 A1 Apr. 20, 2023

Related U.S. Application Data

(60) Provisional application No. 63/257,181, filed on Oct. 19, 2021.

(51) Int. Cl.

| | |
|---|---|
| ***G01N 35/00*** | (2006.01) |
| ***B03C 1/28*** | (2006.01) |
| ***G01N 33/543*** | (2006.01) |

(52) U.S. Cl.

CPC ......... *G01N 35/0098* (2013.01); *B03C 1/288* (2013.01); *G01N 33/54326* (2013.01); *B03C 2201/18* (2013.01); *B03C 2201/26* (2013.01)

(58) Field of Classification Search

None

See application file for complete search history.

(56) References Cited

U.S. PATENT DOCUMENTS

| | | | | |
|---|---|---|---|---|
| 6,764,859 | B1 * | 7/2004 | Kreuwel | B03C 1/288 536/25.4 |
| 2008/0057505 | A1 * | 3/2008 | Lin | G01N 33/54346 435/7.25 |
| 2015/0224499 | A1 * | 8/2015 | Wang | B01L 3/502715 435/7.1 |
| 2020/0298251 | A1 | 9/2020 | Hsu et al. | |

FOREIGN PATENT DOCUMENTS

| | | | |
|---|---|---|---|
| CN | 101035620 | A | 9/2007 |
| CN | 101203758 | A | 6/2008 |
| CN | 108865879 | A | 11/2018 |
| CN | 110643564 | A | 1/2020 |
| CN | 113164962 | A | 7/2021 |
| TW | 201903147 | A | 1/2019 |

* cited by examiner

*Primary Examiner* — Ann Montgomery

(74) *Attorney, Agent, or Firm* — Li & Cai Intellectual Property (USA) Office

(57) ABSTRACT

A separating apparatus of biosubstance and a separating method of the same are provided. The separating method includes: providing a controller to select a positive separation process or a negative separation process to execute according to types of target biosubstances; providing a pipette pump to inject a first magnetic bead reagent or a second magnetic bead reagent into a sample according to the selected separation process, such that first immunomagnetic beads of the first magnetic bead reagent or second immunomagnetic beads of the second magnetic bead reagent are used for binding to the target biosubstances; providing a magnetic separation rack to enrich the target biosubstances so as to separate the target biosubstances and non-target biosubstances; and providing the pipette pump to separate the target biosubstances and the non-target biosubstances.

7 Claims, 10 Drawing Sheets providing a pressure sensor to detect a pressure change in the pipette pump

S100

SEPARATING APPARATUS OF BIOSUBSTANCE AND SEPARATING METHOD OF THE SAME

CROSS-REFERENCE TO RELATED PATENT APPLICATION

This application claims the benefit of priority to the U.S. Provisional Patent Application Ser. No. 63/257,181 filed on Oct. 19, 2021, which application is incorporated herein by reference in its entirety.

Some references, which may include patents, patent applications and various publications, may be cited and discussed in the description of this disclosure. The citation and/or discussion of such references is provided merely to clarify the description of the present disclosure and is not an admission that any such reference is "prior art" to the disclosure described herein. All references cited and discussed in this specification are incorporated herein by reference in their entireties and to the same extent as if each reference was individually incorporated by reference.

FIELD OF THE DISCLOSURE

The present disclosure relates to a separating apparatus of biosubstance and a separating method of the same, and more particularly to a separating apparatus of biosubstance and a separating method of the same utilizing immunomagnetic beads for a separation process.

BACKGROUND OF THE DISCLOSURE

As one of the more novel and significant methods of cancer detection in the related art, liquid biopsy is a personalized, precise, and non-invasive testing method for cancer diagnosis.

Liquid biopsy is a separating method for isolating and enriching target biosubstances (such as cells and nucleic acids) from a sample (such as blood). Generally, the separating method includes: a positive separation process, in which the target biosubstances to be detected (such as circulating tumor cells) are directly separated by reagents; and a negative separation process, in which other biosubstances (such as white blood cells) are removed, leaving the biosubstances to be detected.

However, in the positive separation process, an isolating process may fail to capture or isolate most of the biosubstances to be detected, which may result in a false test result (such as false negatives). On the other hand, in the negative separation process, a residual solution after separation may include many impurities in addition to the biosubstances to be detected. In some cases, the separation process may even damage some of the biosubstances to be detected, which is detrimental to subsequent detection and analysis processes. Furthermore, an existing separating apparatus can only adopt a single separation method, and cannot switch between the positive and negative separation processes according to user requirements. Therefore, there is a need in the related art for a technical solution that addresses the above-mentioned drawbacks.

SUMMARY OF THE DISCLOSURE

In response to the above-referenced technical inadequacies, the present disclosure provides a separating apparatus of biosubstance and a separating method of the same.

In one aspect, the present disclosure provides a separating apparatus of biosubstance. The separating apparatus includes a carrier, a plurality of magnetic separation racks, a pipette, and a controller. The carrier includes a plurality of accommodating regions. Each of the accommodating regions is used for placing a first test tube containing a sample and a second test tube containing a magnetic bead reagent. The sample includes a plurality of target biosubstances and a plurality of non-target biosubstances. The magnetic bead reagent includes a plurality of immunomagnetic beads. The immunomagnetic beads are used for binding to the target biosubstances. The magnetic separation racks are respectively disposed in the accommodating regions. Each of the magnetic separation racks is used to magnetically attract the immunomagnetic beads. The pipette is disposed on the carrier and moves between the accommodating regions. The pipette includes a pipette pump, and the pipette pump is used to perform the action of suction and injection. The controller is electrically connected to the carrier and the pipette. The controller is used to control the operation of the carrier and the pipette. The controller selects between different separation processes to execute, according to types of the target biosubstances, so as to isolate the target biosubstances from the sample.

In another aspect, the present disclosure provides a separating method of biosubstance. The separating method is used for processing a sample containing target biosubstances and non-target biosubstances. The separating method includes: providing a controller to select a positive separation process or a negative separation process to execute, according to types of the target biosubstances; providing a pipette pump to inject a first magnetic bead reagent or a second magnetic bead reagent into the sample according to the selected separation process, such that first immunomagnetic beads of the first magnetic bead reagent or second immunomagnetic beads of the second magnetic bead reagent binds to the target biosubstances, when the controller executes the positive separation process, the pipette pump is used to inject the first magnetic bead reagent into the sample, and when the controller executes the negative separation process, the pipette pump is used to inject the second magnetic bead reagent into the sample; providing a magnetic separation rack to generate a magnetic field to enrich the target biosubstances, so as to separate the target biosubstances and the non-target biosubstances; providing the pipette pump to separate the target biosubstances and the non-target biosubstances, when the controller executes the positive separation process, the pipette pump is used to suction and capture the target biosubstances, and when the controller executes the negative separation process, the pipette pump is used to suck away and remove the non-target biosubstances and leave the target biosubstances.

Therefore, in the separating apparatus of biosubstance and the separating method of the same provided by the present disclosure, by virtue of "the immunomagnetic beads being used for binding to the target biosubstances," "the magnetic separation rack being used to magnetically attract the immunomagnetic beads," and "the controller selecting between different separation processes to execute according to types of the target biosubstances so as to isolate the target biosubstances from the sample," users can choose the appropriate separation process to achieve the purpose of enriching biosubstances. Furthermore, the separation process can be implemented through automated devices, thereby reducing a number of manual steps and improving the reproducibility and accuracy of detection.

These and other aspects of the present disclosure will become apparent from the following description of the embodiment taken in conjunction with the following drawings and their captions, although variations and modifications therein may be affected without departing from the spirit and scope of the novel concepts of the disclosure.

BRIEF DESCRIPTION OF THE DRAWINGS

The described embodiments may be better understood by reference to the following description and the accompanying drawings, in which.

DETAILED DESCRIPTION OF THE EXEMPLARY EMBODIMENTS

Figure 1:
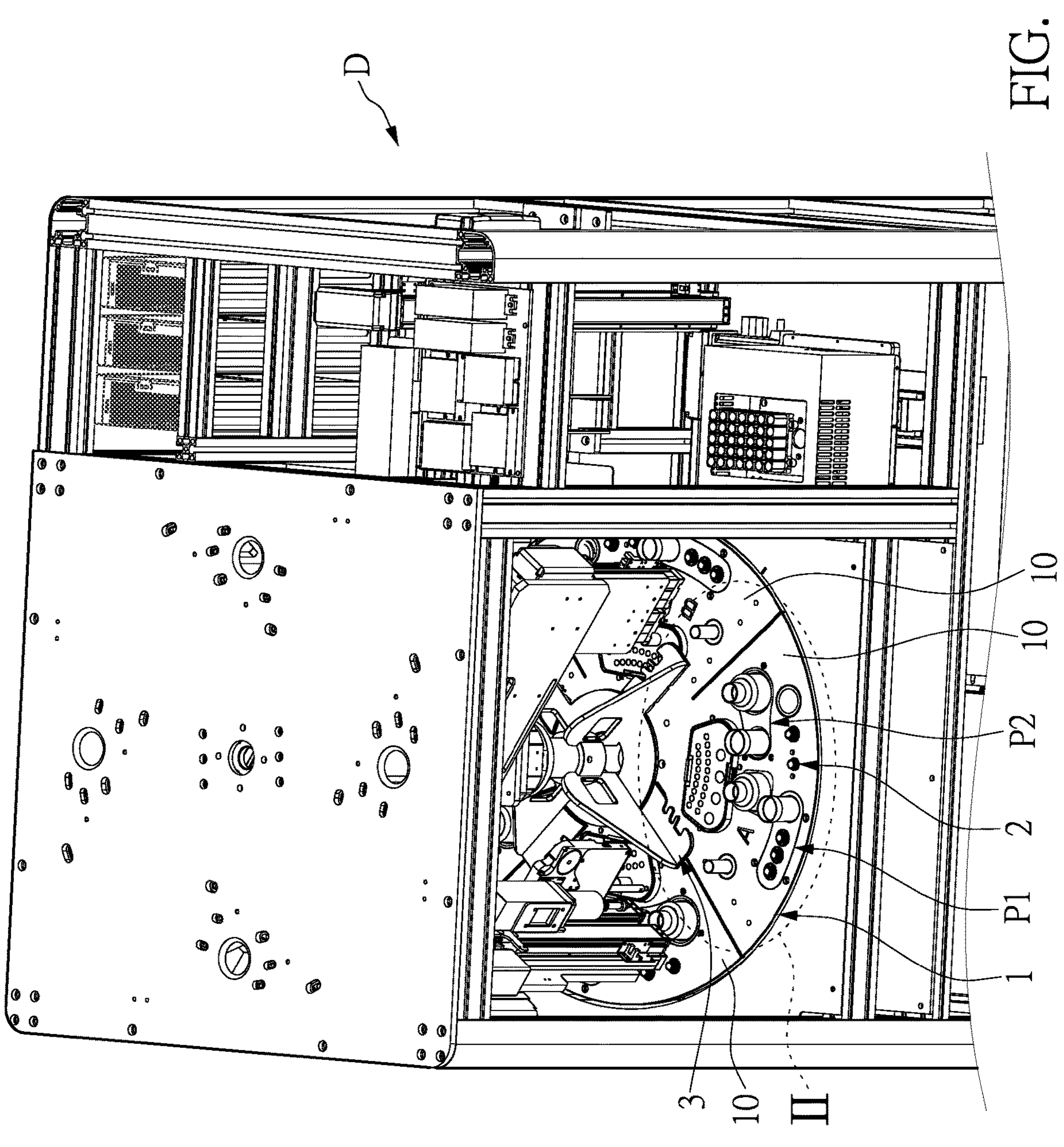
FIG. 1 is a schematic view of a separating apparatus of biosubstance according to the present disclosure.

The present disclosure is more particularly described in the following examples that are intended as illustrative only since numerous modifications and variations therein will be apparent to those skilled in the art. Like numbers in the drawings indicate like components throughout the views. As used in the description herein and throughout the claims that follow, unless the context clearly dictates otherwise, the meaning of “a”, “an”, and “the” includes plural reference, and the meaning of “in” includes “in” and “on”. Titles or subtitles can be used herein for the convenience of a reader, which shall have no influence on the scope of the present disclosure.

The terms used herein generally have their ordinary meanings in the art. In the case of conflict, the present document, including any definitions given herein, will prevail. The same thing can be expressed in more than one way. Alternative language and synonyms can be used for any term(s) discussed herein, and no special significance is to be placed upon whether a term is elaborated or discussed herein. A recital of one or more synonyms does not exclude the use of other synonyms. The use of examples anywhere in this specification including examples of any terms is illustrative only, and in no way limits the scope and meaning of the present disclosure or of any exemplified term. Likewise, the present disclosure is not limited to various embodiments given herein. Numbering terms such as “first”, “second” or “third” can be used to describe various components, signals or the like, which are for distinguishing one component/signal from another one only, and are not intended to, nor should be construed to impose any substantive limitations on the components, signals or the like.

EMBODIMENTS

Figure 2:
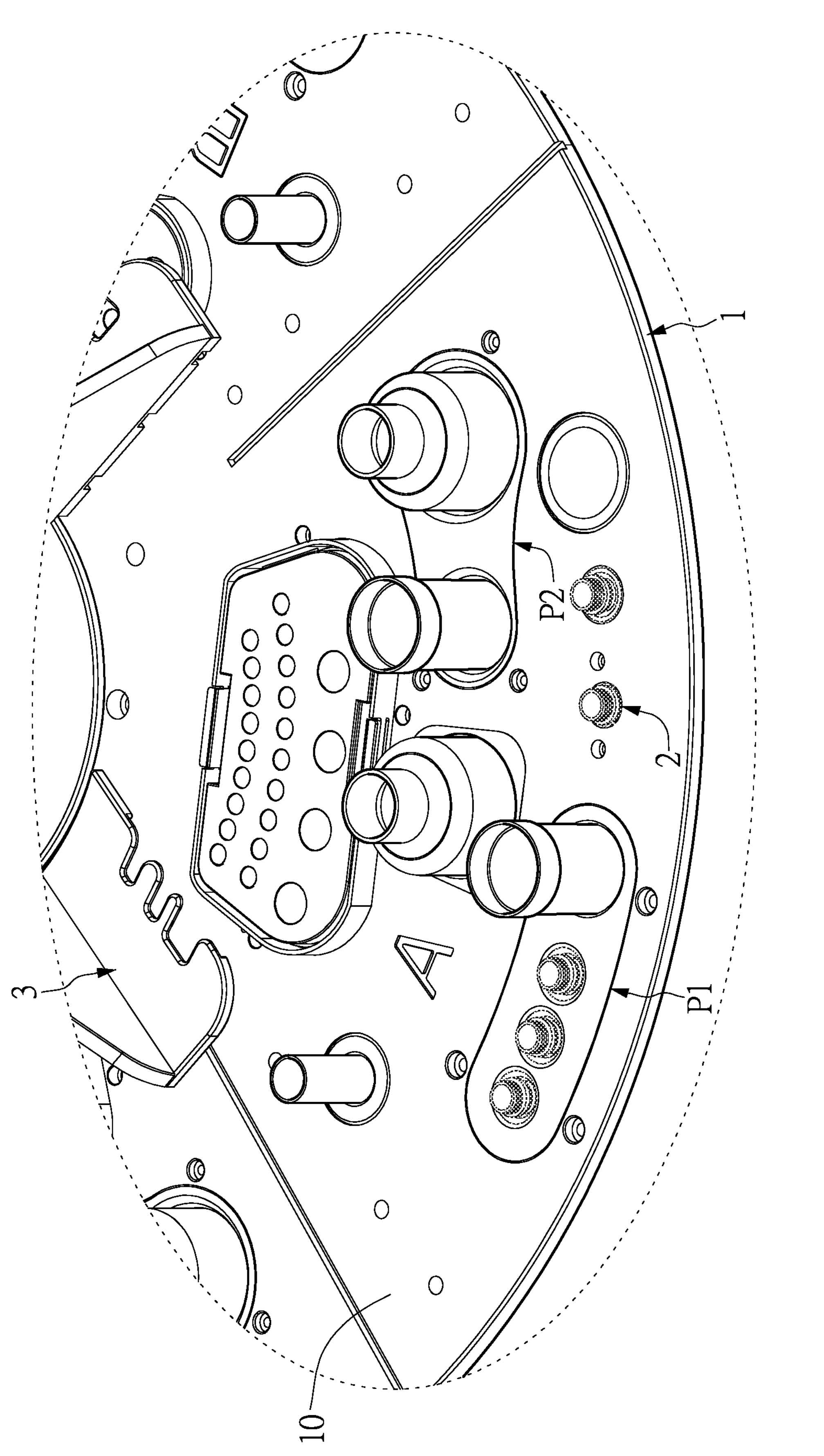
FIG. 2 is a schematic enlarged view of part II of FIG. 1.
Figure 3:
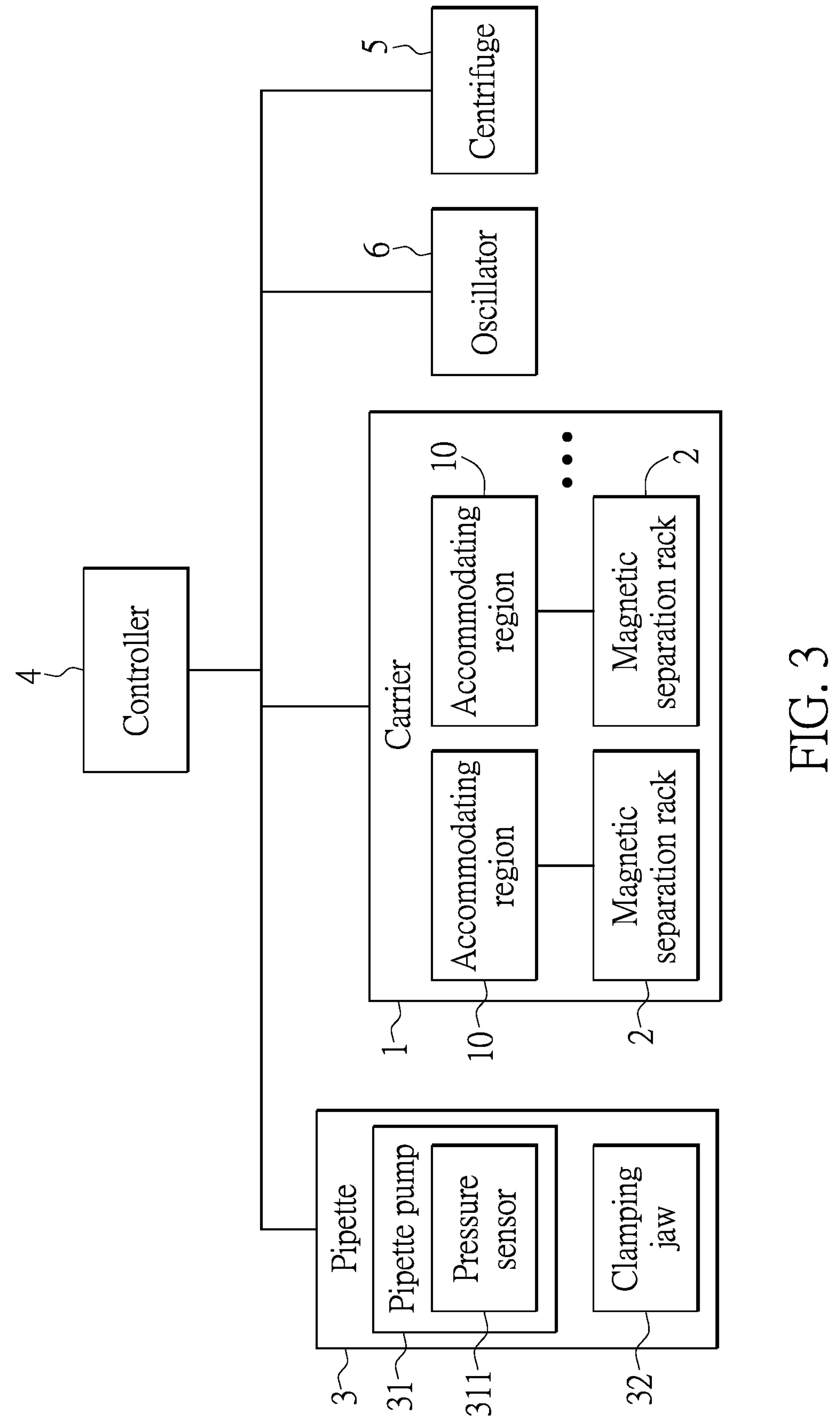
FIG. 3 is a functional block diagram of the separating apparatus of biosubstance according to the present disclosure.

Referring to FIG. 1 to FIG. 3, the present disclosure provides a separating apparatus D of biosubstance. The separating apparatus D includes a carrier 1, a plurality of magnetic separation racks 2, a pipette 3, and a controller 4. The carrier 1 includes a plurality of accommodating regions 10. The magnetic separation racks 2 are respectively disposed in the accommodating regions 10. For example, in one embodiment of the present disclosure, the carrier 1 can be a rotating disk, and the rotating disk is equally divided into four fan-shaped areas (i.e., four accommodating regions 10). Each fan-shaped area has one magnetic separation rack 2 provided thereon, but the present disclosure is not limited thereto. Moreover, each accommodating region 10 includes a test tube area P1 and a reagent area P2. The test tube area P1 can be used for placing a test tube containing a sample, and the reagent area P2 can be used for placing a test tube containing a magnetic bead reagent having a plurality of immunomagnetic beads.

The magnetic separation racks 2 are respectively disposed in the accommodating regions 10. Each of the magnetic separation racks 2 includes at least one magnet 24, and each of the magnetic separation racks 2 is used to magnetically attract the immunomagnetic beads. The pipette 3 is disposed on the carrier 1 and moves between the accommodating regions 10. The pipette 3 includes a pipette pump 31 and a clamping jaw 32. The pipette pump 31 is used to perform the action of suction and injection. The clamping jaw 32 is used to move the test tube to different positions.

In addition, as shown in FIG. 3, the separating apparatus D further includes a centrifuge 5 and an oscillator 6. The centrifuge 5 and the oscillator 6 are electrically connected to the controller 4, such that the controller 4 is used to control the operation of the centrifuge 5 and the oscillator 6.

Figure 6:
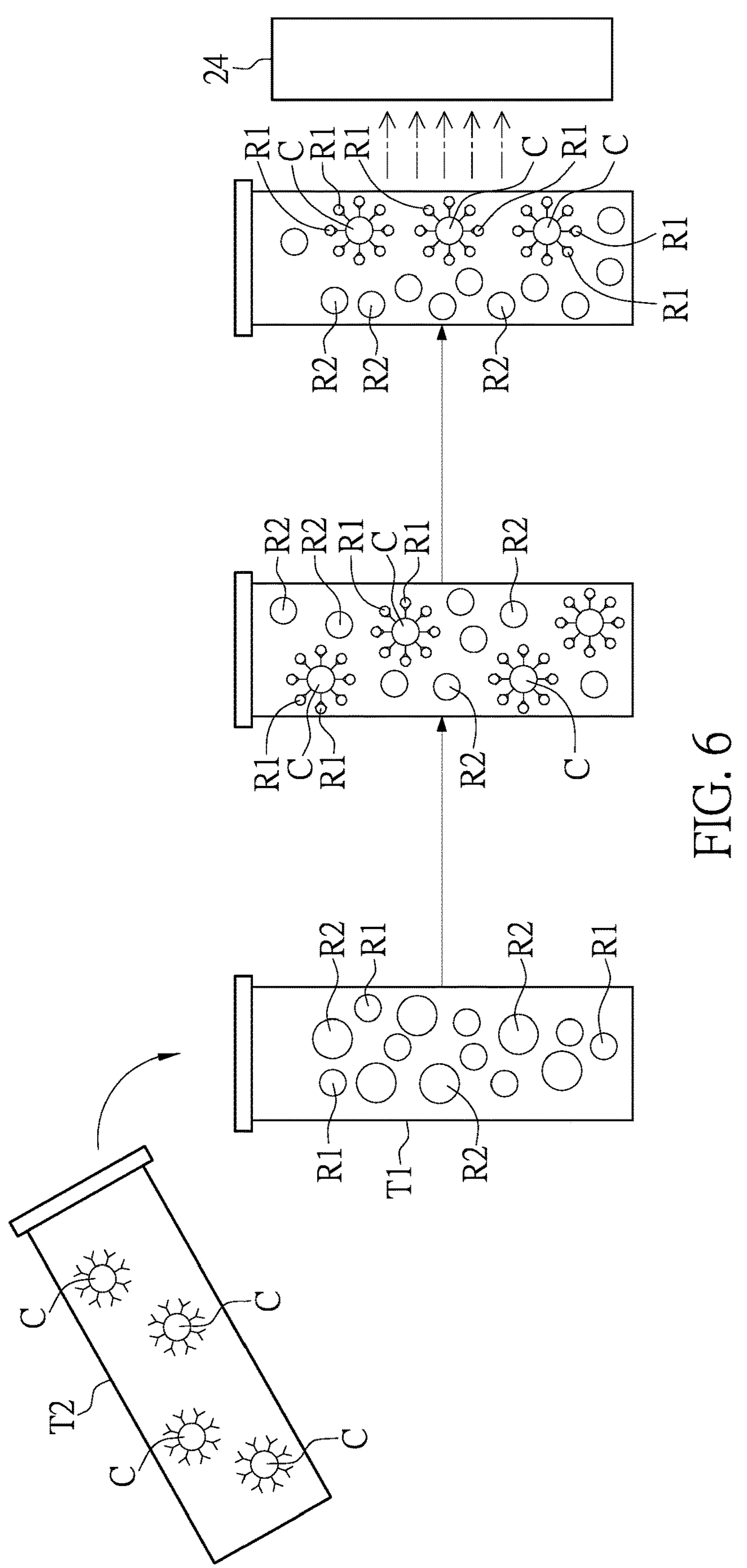
FIG. 6 is a schematic view of immunomagnetic beads binding to target biosubstances according to the present disclosure.

The sample may include human body fluids, such as pleural effusion, hydropericardium, ascites, urine, semen, plasma, blood, and cerebrospinal fluid, but the present disclosure is not limited thereto. The magnetic bead reagent includes a plurality of immunomagnetic beads (IMBs). The immunomagnetic beads can be used for binding to specific biosubstances in the sample. Specifically, the biosubstances in the sample can be divided into target biosubstances and non-target biosubstances according to types of biosubstances to be captured. Referring to FIG. 2 and FIG. 6, in one of the accommodating regions 10, a first test tube T1 located in the test tube area P1 contains a sample, and the sample includes a target biosubstance R1 and a non-target biosubstance R2. A second test tube T2 located in the reagent area P2 contains a magnetic bead reagent, and the magnetic bead reagent contains immunomagnetic beads C. As shown in FIG. 6, the pipette pump is used to suction the magnetic bead reagent from the second test tube T2, and then injects the magnetic bead reagent into the first test tube T1, such that the target biosubstances R1 can be bound to the immunomagnetic beads C in the magnetic bead reagent. Then, the first test tube T1 is moved from the test tube area P1 to the magnetic separation rack 2 by the clamping jaw 32. Under the magnetic attraction of the at least one magnet 24 of the magnetic separation rack 2 (the broken-line arrow in FIG. 6 is used to indicate the magnetic attraction direction of the at least one magnet 24), the immunomagnetic beads C that is bound to the target biolosubstances R1 is enriched in the first test tube T1 at one side of the first test tube T1 adjacent to the at least one magnet 24. In other words, the target biosubstances R1 is enriched to be separated from the non-target biosubstances R2.

It is worth mentioning that, the pipette pump 31 includes a pressure sensor 311. When the sample is sucked by the pipette pump 31 from the first test tube T1, the pressure sensor 311 is used to detect a pressure change in the pipette pump 31.

Figure 4:
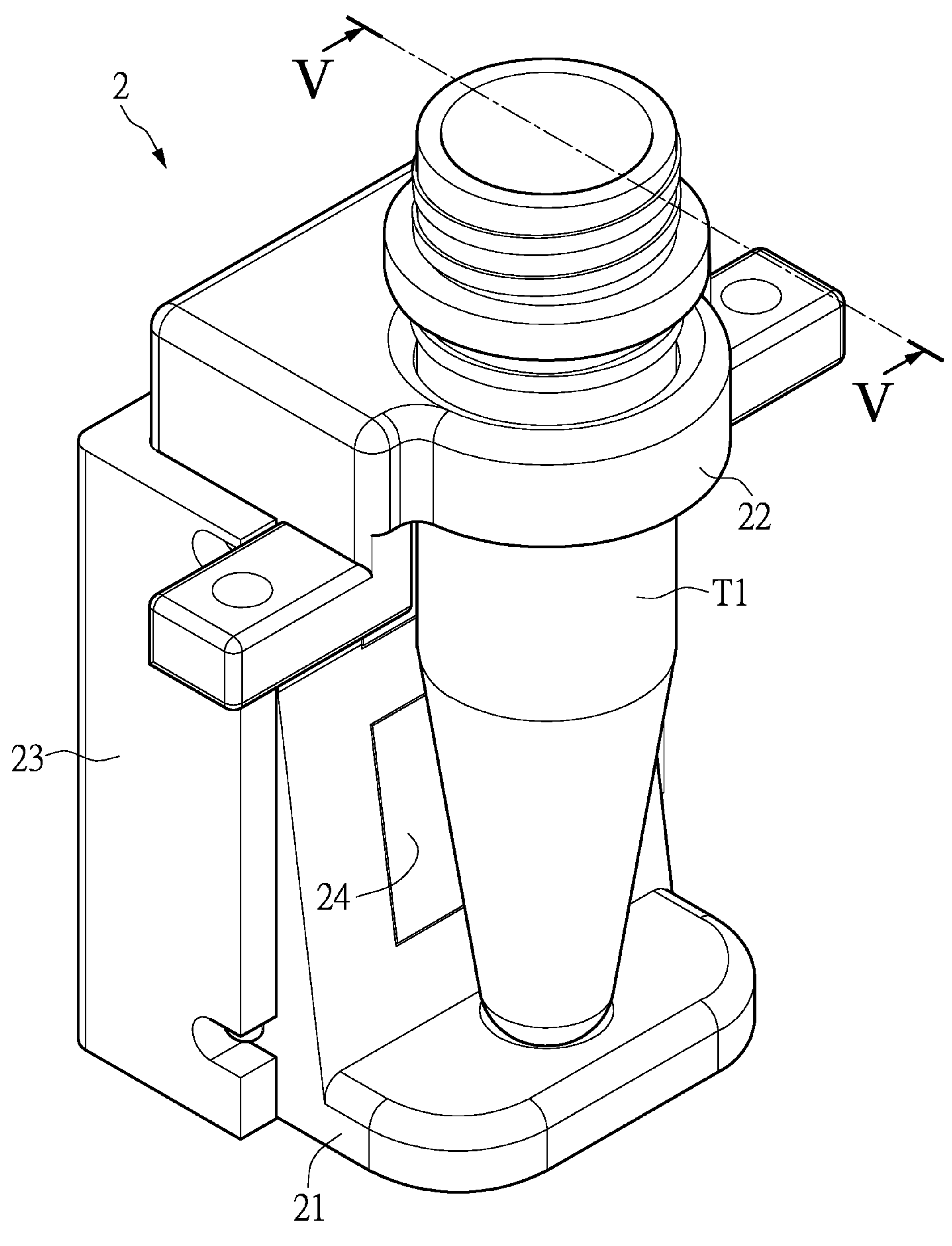
FIG. 4 is a schematic view of a magnetic separation rack according to the present disclosure.
Figure 5:
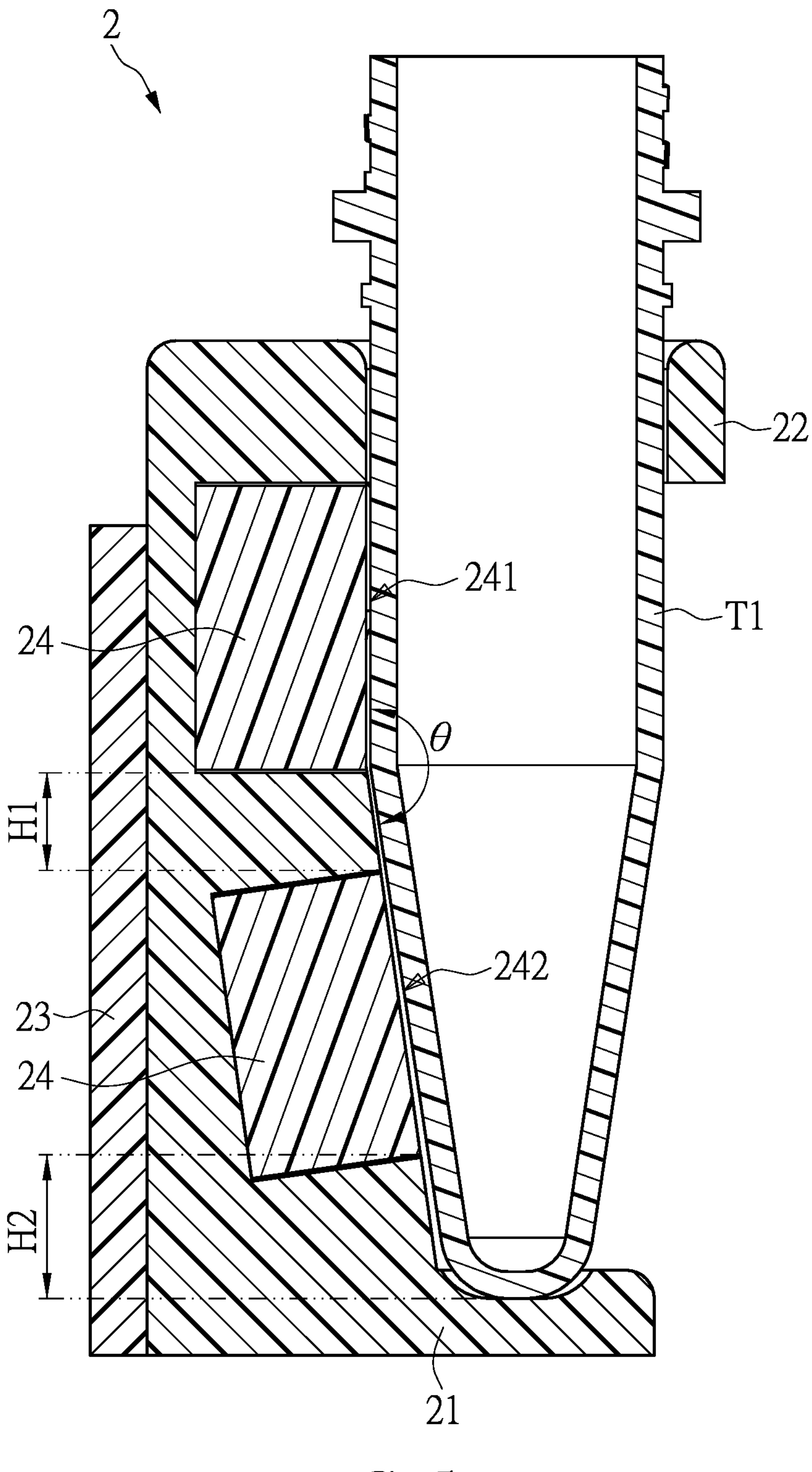
FIG. 5 is a schematic cross-sectional view taken along line V-V of FIG. 4.

Referring to FIG. 4 and FIG. 5, in the present disclosure, each of the magnetic separation racks 2 includes a rack base 21, a tube holder 22, a metal shield 23, and two magnets 24. The tube holder 22 is fixed on the rack base 21. The tube holder 22 is used to hold the first test tube T1 in a vertical position. The two magnets 24 are disposed on the rack base 21 and adjacent to each other. It should be noted that, the present disclosure is not limited to a quantity of the magnets 24. Furthermore, two magnetic attraction surfaces 241 and 242 of the two magnets 24 (closer to a surface of the first test tube T1) have an included angle θ therebetween, and the included angle θ ranges from 90 degrees to 180 degrees. Preferably, the included angle θ is 172 degrees, which enables the two magnetic attraction surfaces 241 and 242 to better fit with the shape of an outer contour of the first test tube T1. Moreover, the two magnets 24 are spaced apart from each other by a gap H1. The lower magnet 24 of the two magnets 24 and the bottom of the first test tube T1 have a gap H2 therebetween. The gaps H1 and H2 range from 2.5 mm to 5.5 mm. Preferably, the gap H1 ranges from 2.5 mm to 4 mm. More preferably, the gap H1 substantially is 3.5 mm and the gap H2 substantially is 5 mm. In addition, the two magnets 24 have opposite magnetic properties. For example, in one embodiment, the polarity of the magnetic attraction surface 241 of the upper magnet 24 is S pole, and the polarity of the magnetic attraction surface 242 of the lower magnet 24 is N pole. The metal shield 23 is disposed on the rack base 21. In particular, the metal shield 23 of the magnetic separation rack 2 faces the center of the rotating disk (i.e., the carrier 1) so as to block the magnetic field of the magnetic separation rack 2. In other words, the metal shield 23 prevent magnetic fields of the four magnetic separation racks 2 from interfering with each other. Compared with the conventional magnetic separation rack having only one magnet, the magnetic separation rack 2 of the present disclosure can significantly enhance the magnetic field generated by the two magnets 24 through the configuration of the two magnets 24 and the design of the gaps H1 and H2.

Reference is further made to FIG. 3, in which the controller 4 is electrically connected to the carrier 1 and the pipette 3 and is used to control the operation of the carrier 1 and the pipette 3. The controller 4 selects different separation processes to execute according to types of the target biosubstances R1 so as to isolate the target biosubstances R1 from the sample. Specifically, the controller 4 selects a positive separation process or a negative separation process to execute according to the types of the target biosubstances R1. For example, when the target biosubstances R1 includes circulating tumor cells (CTCs), circulating tumor DNA (ctDNA), or microRNA (miRNA), the controller 4 executes the positive separation process. When the target biosubstances R1 includes white blood cells (WBCs), the controller 4 executes the negative separation process. However, in the present disclosure, the types of the target biosubstances R1 are not limited to CTCs, ctDNA, miRNA, and WBCs.

Accordingly, when the controller 4 executes the positive separation process, the pipette pump 31 is used to suction and capture the target biosubstances R1. When the controller 4 executes the negative separation process, the pipette pump 31 is used to suck away and remove the non-target biosubstances R2 and leave the target biosubstances R1. In addition, the controller 4 is used to adjust parameters of the pipette 3, the centrifuge 5, and the oscillator 6 according to one of the separation processes performed. The parameters include a speed and a volume of suction and injection of the pipette pump 31, a standing time of the first test tube T1 in the magnetic separation rack 2, and a rotation speed and a rotation time of the centrifuge 5 and the oscillator 6.

Figures 8, 9:
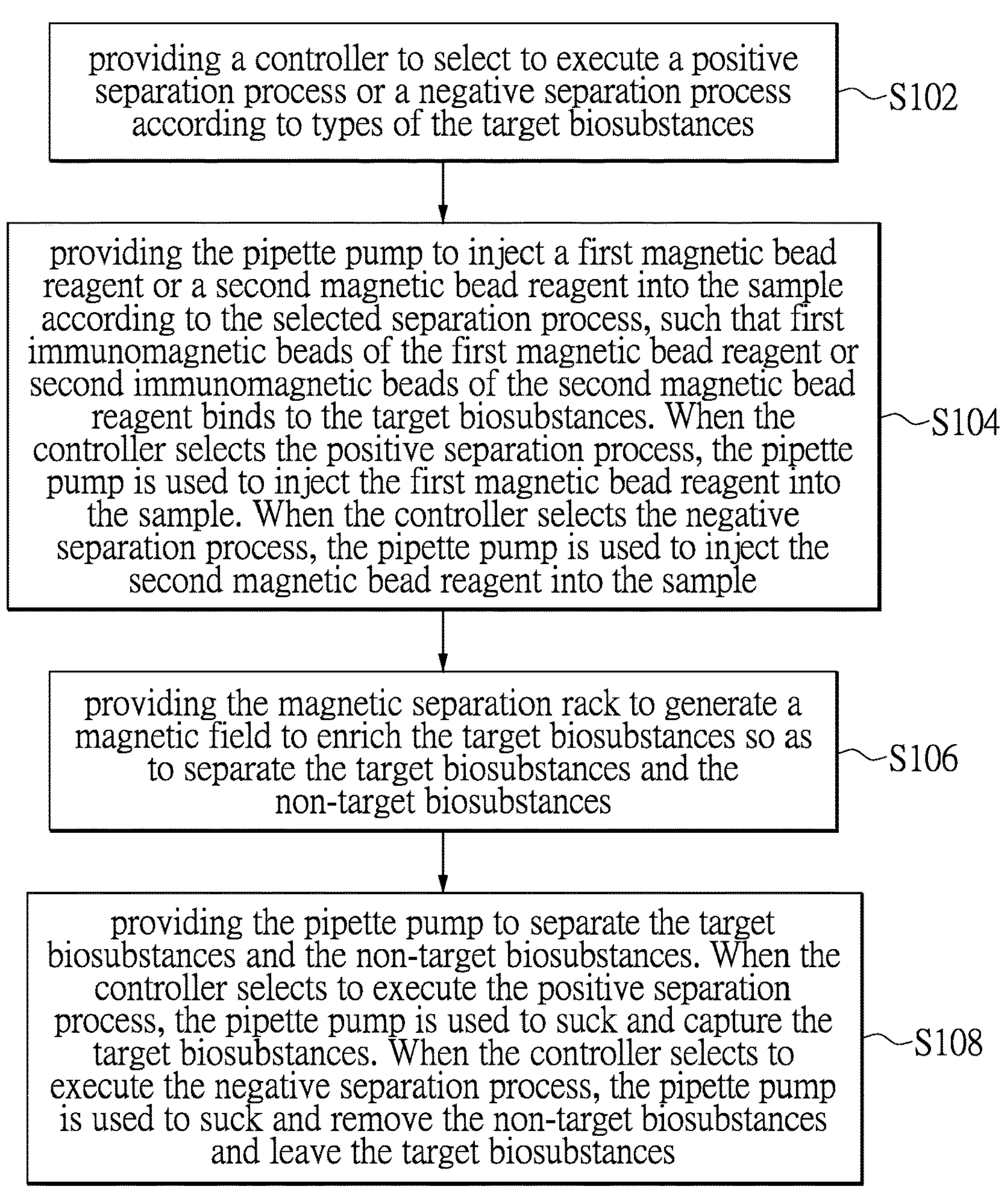
FIG. 8 is a schematic view of step S102 to step S108 of a separating method of biosubstance according to the present disclosure.
FIG. 9 is a schematic view of step S100 of the separating method of biosubstance according to the present disclosure.

Referring to FIG. 8 and FIG. 9, the present disclosure provides a separating method of biosubstance that can be performed by the separating apparatus D of biosubstance provided by the present disclosure. The separating method at least includes steps as follows (as shown in FIG. 3 and FIG. 6).

Step S102: providing a controller 4 to select the positive separation process or the negative separation process to execute according to the types of the target biosubstances R1.

Specifically, when the target biosubstances R1 includes circulating tumor cells (CTCs), circulating tumor DNA (ctDNA), or microRNA (miRNA), the controller 4 executes the positive separation process. When the target biosubstances R1 includes white blood cells (WBCs), the controller 4 executes the negative separation process.

Step S104: providing the pipette pump 31 to inject a first magnetic bead reagent or a second magnetic bead reagent into the sample according to the selected separation process, such that first immunomagnetic beads of the first magnetic bead reagent or second immunomagnetic beads of the second magnetic bead reagent binds to the target biosubstances. When the controller 4 executes the positive separation process, the pipette pump 31 is used to inject the first magnetic bead reagent into the sample. When the controller 4 executes the negative separation process, the pipette pump 31 is used to inject the second magnetic bead reagent into the sample.

Step S106: providing the magnetic separation rack 2 to generate a magnetic field to enrich the target biosubstances R1 so as to separate the target biosubstances R1 and the non-target biosubstances R2.

Step S108: providing the pipette pump 31 to separate the target biosubstances R1 and the non-target biosubstances R2. When the controller 4 executes the positive separation process, the pipette pump 31 is used to suction and capture the target biosubstances R1. When the controller 4 executes the negative separation process, the pipette pump 31 is used to suck away and remove the non-target biosubstances R2 and leave the target biosubstances R1.

The separating method of biosubstance further includes:

Step S100: providing a pressure sensor 311 to detect a pressure change in the pipette pump 31.

The step S100 is performed before the controller 4 selects the positive separation process or the negative separation process to execute. The pressure sensor 311 stores in advance a threshold value of the pressure change in the pipette pump 31. If foreign bodies are generated in the sample, such as when clots are generated in blood, the pipette pump 31 sucks the foreign bodies while sucking the sample, and then the pressure sensor 311 detects the pressure change in the pipette pump 31. When the pressure change exceeds the threshold value, the pressure sensor 311 outputs a sensing signal to the controller 4, and the controller 4 stops controlling the actions of the relevant components accordingly. In other words, when qualitative change has occurred in the sample, the controller 4 can stop subsequent operations in time to avoid waste of materials and time.

Figure 10:
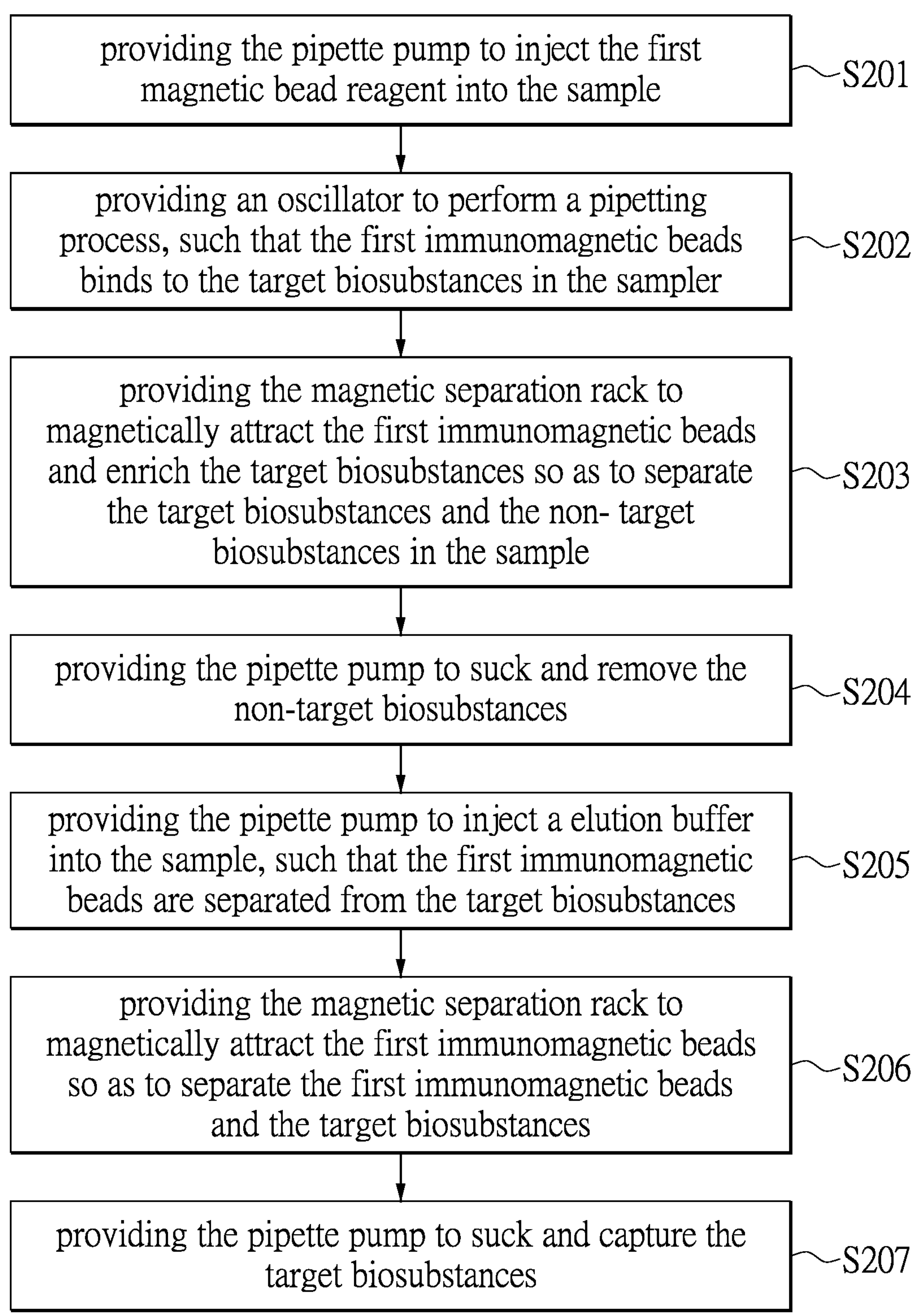
FIG. 10 is a schematic view of step S201 to step S207 of a positive separation process of the separating method of biosubstance according to the present disclosure.

Referring to FIG. 10, the positive separation process at least includes steps as follows (as shown in FIG. 3 and FIG. 6).

Step S201: providing the pipette pump 31 to inject the first magnetic bead reagent into the sample.

Step S202: providing an oscillator 6 to perform a mixing process, such that the first immunomagnetic beads binds to the target biosubstances R1 in the sample.

Step S203: providing the magnetic separation rack 2 to magnetically attract the first immunomagnetic beads and enrich the target biosubstances R1 so as to separate the target biosubstances R1 and the non-target biosubstances R2 in the sample.

Figure 7:
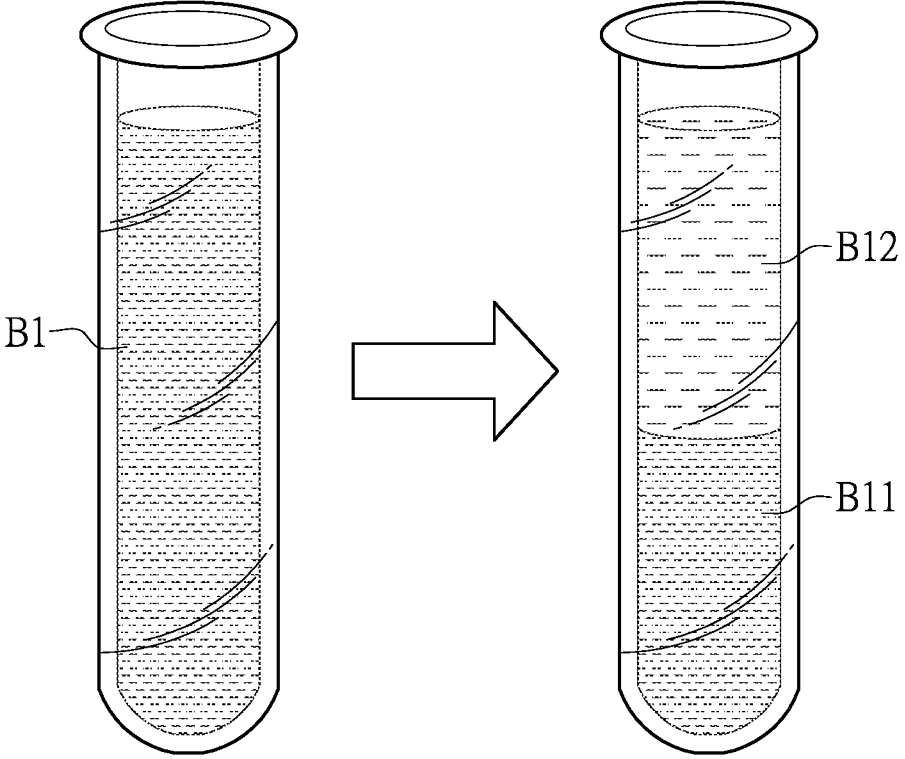
FIG. 7 is a schematic view of a sample separation according to the present disclosure.

Referring to FIG. 7, in steps S201 to S203, the sample B1 can be divided into sample liquid B11 below and supernatant liquid B12 above after the action of the oscillator 6 and the magnetic separation rack 2. It should be noted that, the sample liquid B11 contains the first immunomagnetic beads in the first magnetic bead reagent, and the target biolsubstances (such as CTC, ctDNA, or miRNA) that are bound to the first immunomagnetic beads. The supernatant liquid B12 contains impurities that are mainly substances other than the first immunomagnetic beads and the target biosubstances in the sample B1.

Furthermore, in steps S201 to S203, a washing buffer is added into the first test tube T1 containing the sample B1, and then the pipette pump 31 performs continuous pipetting to the first test tube T1 containing the sample B1 with the washing buffer. The continuous pipetting indicates that the liquid (i.e., the sample B1 with the washing buffer) in the first test tube T1 is sucked in and then spit out continuously by the pipette pump 31. Accordingly, the liquid in the first test tube T1 can be disturbed from impact, thereby preventing precipitation from occurring, and promoting the mixed effect of the sample B1 and the washing buffer.

Step S204: providing the pipette pump 31 to suck away and remove the non-target biosubstances R2.

Step S205: providing the pipette pump 31 to inject an elution buffer into the sample B1, such that the first immunomagnetic beads are separated from the target biosubstances R1.

Step S206: providing the magnetic separation rack 2 to magnetically attract the first immunomagnetic beads so as to separate the first immunomagnetic beads and the target biosubstances R1.

Step S207: providing the pipette pump 31 to suction and capture the target biosubstances R1.

In the above-mentioned positive separation process, usage counts of the pipette pump 3, the centrifuge 5, and the oscillator 6 are not limited, and the users can select appropriate devices in appropriate steps according to practical requirements.

In another embodiment of the present disclosure, when the sample B1 is a blood sample and the target biosubstances R1 are ctDNA or miRNA, before the step S201, the centrifuge 5 can be used to perform the purification process to extract blood plasma from the blood sample. After the clamping jaw 32 moves the test tube containing the blood sample from the test tube area P1 to the centrifuge 5, the centrifuge 5 can use the centrifugal force generated by the high-speed rotation to accelerate the sedimentation speed of the biosubstances in the sample, and separate biosubstances having different sedimentation coefficients and density masses in the blood sample to achieve the purpose of purification. Therefore, through the purification process performed by the centrifuge 5, the blood plasma can be separated from the blood sample.

Figure 11:
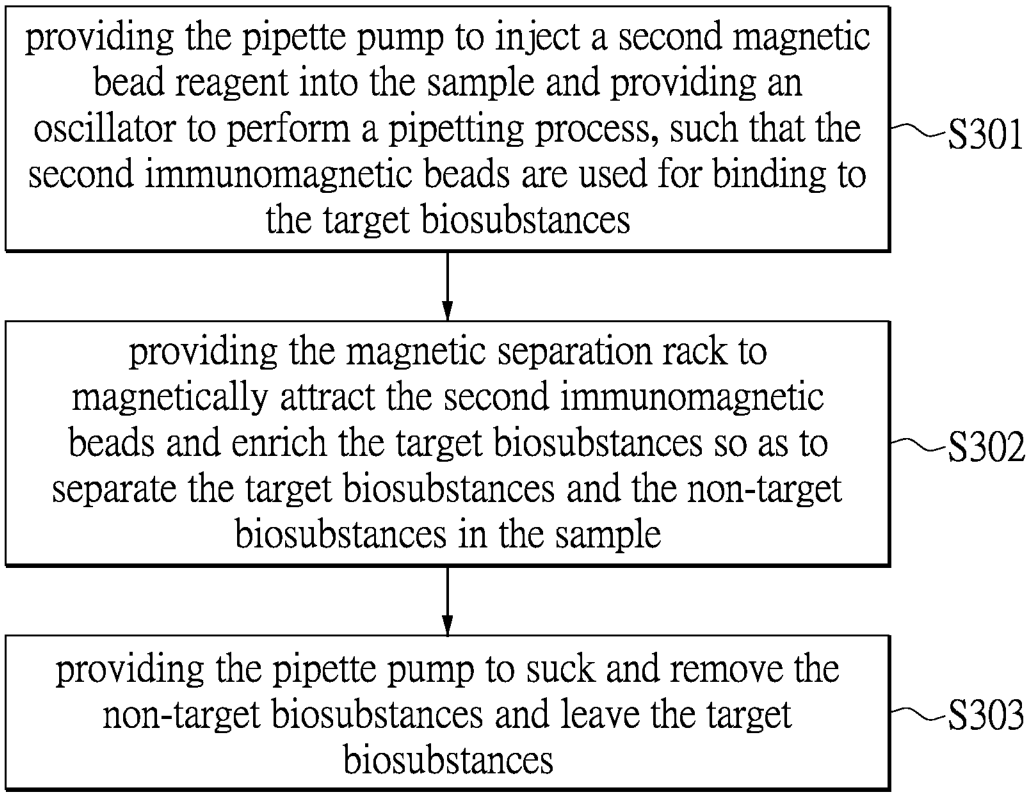
FIG. 11 is a schematic view of step S301 to step S304 of a negative separation process of the separating method of biosubstance according to the present disclosure.

Referring to FIG. 11, in the negative separation process, the target biosubstances are WBCs, and the non-target biosubstances are CTC, ctDNA, or miRNA, but the present disclosure is not limited thereto. The negative separation process at least includes steps as follows (as shown in FIG. 3 and FIG. 6).

Step S301: providing the pipette pump 31 to inject a second magnetic bead reagent into the sample B1 and providing an oscillator 6 to perform a mixing process, such that the second immunomagnetic beads binds to the target biosubstances R1 (such as WBCs).

Step S302: providing the magnetic separation rack 2 to magnetically attract the second immunomagnetic beads and enrich the target biosubstances R1 so as to separate the target biosubstances R1 and the non-target biosubstances R2 in the sample.

Step S303: providing the pipette pump 31 to suck away and remove the non-target biosubstances R2 (such as CTC, ctDNA, or miRNA) and leave the target biosubstances R1.

In another embodiment of the present disclosure, when the sample is a blood sample and the target biosubstances R1 are WBCs, before the step S301, the pipette pump 31 can be used to inject a lysis buffer into the sample to perform a lysis process so as to lyse red blood cells in the non-target biolosubstances R2.

The lysis process is used for the purpose of removing the red blood cells in the blood sample. In this step, the pipette pump 31 can be appropriately used for continuous pipetting and the centrifuge 5 can be appropriately used for purification, but the present disclosure is not limited thereto. In addition, after lysis process, the contents of the non-target biosubstances R2 mainly include CTCs.

In the negative separation process, a buffer can be appropriately added at each step. The functions of the buffer at different steps can be the same or different. The buffer can be used for washing, diluting, and resuspension, such that the sample B1 is prompted to form the sample liquid B11 and the supernatant liquid B12 (as shown in FIG. 7), and the contents of the supernatant liquid B12 formed in each step can be the same or different. In the above-mentioned negative separation process, usage counts of the pipette pump 3, the centrifuge 5 and the oscillator 6 are not limited, and the users can select appropriate devices in appropriate steps according to practical requirements.

Beneficial Effects of the Embodiments

In conclusion, in the separating apparatus of biosubstance and the separating method of the same provided by the present disclosure, by virtue of "the immunomagnetic beads being used for binding to the target biosubstances," "the magnetic separation rack being used to magnetically attract the immunomagnetic beads," and "the controller selecting between different separation processes to execute according to types of the target biosubstances so as to isolate the target biosubstances from the sample," the users can choose the appropriate separation process to achieve the purpose of enriching biosubstances. Furthermore, the separation process can be implemented through automated devices, thereby reducing manual steps and improving the reproducibility and accuracy of detection.

The foregoing description of the exemplary embodiments of the disclosure has been presented only for the purposes of illustration and description and is not intended to be exhaustive or to limit the disclosure to the precise forms disclosed. Many modifications and variations are possible in light of the above teaching.

The embodiments were chosen and described in order to explain the principles of the disclosure and their practical application so as to enable others skilled in the art to utilize the disclosure and various embodiments and with various modifications as are suited to the particular use contemplated. Alternative embodiments will become apparent to those skilled in the art to which the present disclosure pertains without departing from its spirit and scope.

What is claimed is:

1. A separating method of biosubstance for processing a sample contained in a test tube, the sample including target biosubstances and non-target biosubstances, the separating method comprising:

providing a controller to select a positive separation process or a negative separation process to execute according to types of the target biosubstances;

providing a pipette pump to inject a first magnetic bead reagent or a second magnetic bead reagent into the sample according to the selected separation process, such that first immunomagnetic beads of the first magnetic bead reagent or second immunomagnetic beads of the second magnetic bead reagent binds to the target biosubstances; wherein, when the controller executes the positive separation process, the pipette pump is used to inject the first magnetic bead reagent into the sample, and when the controller executes the negative separation process, the pipette pump is used to inject the second magnetic bead reagent into the sample;

providing a magnetic separation rack with two magnets having opposite magnetic properties, placing the test tube containing the sample on the magnetic separation rack such that the two magnets are arranged along a sidewall of the test tube with magnetic attraction surfaces facing toward the test tube, and applying a magnetic field to the sample by the two magnets to enrich the target biosubstances and separate the target biosubstances and the non-target biosubstances; and providing the pipette pump to separate the target biosubstances and the non-target biosubstances, wherein, when the controller executes the positive separation process, the pipette pump is used to suction and capture the target biosubstances, and when the controller executes the negative separation process, the pipette pump is used to suck away and remove the non-target biosubstances and leave the target biosubstances.

2. The separating method according to claim 1, wherein the positive separation process includes:

providing the pipette pump to inject the first magnetic bead reagent into the sample;

providing an oscillator to perform a mixing process, such that the first immunomagnetic beads binds to the target biosubstances in the sample;

providing the magnetic separation rack to magnetically attract the first immunomagnetic beads and enrich the target biosubstances so as to separate the target biosubstances and the non-target biosubstances in the sample;

providing the pipette pump to suck and remove the non-target biosubstances;

providing the pipette pump to inject a elution buffer into the sample, such that the first immunomagnetic beads are separated from the target biosubstances;

providing the magnetic separation rack to magnetically attract the first immunomagnetic beads so as to separate the first immunomagnetic beads and the target biosubstances; and providing the pipette pump to suck and capture the target biosubstances.

3. The separating method according to claim 1, wherein the negative separation process includes:

providing the pipette pump to inject a second magnetic bead reagent into the sample and providing an oscillator to perform a mixing process, such that the second immunomagnetic beads binds to the target biosubstances;

providing the magnetic separation rack to magnetically attract the second immunomagnetic beads and enrich the target biosubstances so as to separate the target biosubstances and the non-target biosubstances in the sample; and providing the pipette pump to suck and remove the non-target biosubstances and leave the target biosubstances.

4. The separating method according to claim 3, wherein, when the sample is blood, the negative separation process further includes:

providing the pipette pump to inject a lysis buffer to the sample for performing a lysis process, so as to lyse red blood cells in the non-target biosubstances.

5. The separating method according to claim 1, wherein, when the target biosubstances include circulating tumor cells (CTCs), circulating tumor DNA (ctDNA), or microRNA (miRNA), the controller executes the positive separation process; wherein, when the target biosubstances include white blood cells (WBCs), the controller executes the negative separation process.

6. The separating method according to claim 1, further comprising:

providing a pressure sensor to detect a pressure change in the pipette pump.

7. The separating method according to claim 1, wherein two surfaces of the two magnets have an included angle therebetween that ranges from 90 degrees to 180 degrees, and the two magnets are spaced apart from each other by a gap that ranges from 2.5 mm to 5.5 mm.

* * * * *